United States Patent [19]

Shutske et al.

[11] Patent Number: 5,037,833
[45] Date of Patent: Aug. 6, 1991

[54] N-[SUBSTITUTED ALKYLIDENE]FUSED-BICYCLOALKYLIDENE QUINOLINAMINES USEFUL FOR ENHANCING THE CHOLINERGIC FUNCTION IN A MAMMAL

[75] Inventors: Gregory M. Shutske, Somerset; Kevin J. Kapples, Little York, both of N.J.

[73] Assignee: Hoechst-Roussel Pharmaceuticals Inc., Somerville, N.J.

[21] Appl. No.: 480,388

[22] Filed: Feb. 15, 1990

Related U.S. Application Data

[63] Continuation-in-part of Ser. No. 223,848, Jul. 25, 1988, abandoned, which is a continuation-in-part of Ser. No. 94,181, Sep. 8, 1987, abandoned.

[51] Int. Cl.$^5$ .................. A61K 31/47; C07D 219/00; C07D 221/22; C07D 471/04
[52] U.S. Cl. ........................ 514/289; 546/74; 546/79; 546/80; 546/81; 546/89; 546/93; 546/82; 514/290; 514/291; 514/292
[58] Field of Search .................... 546/74; 514/289

[56] References Cited

U.S. PATENT DOCUMENTS

| | | | |
|---|---|---|---|
| 3,232,945 | 2/1966 | Sigal, Jr. et al. | 546/93 |
| 3,318,895 | 5/1967 | Pribyl et al. | 546/93 |
| 3,318,896 | 5/1967 | Pribyl et al. | 546/93 X |
| 3,541,066 | 11/1970 | Wolf | 546/63 |
| 3,580,915 | 5/1971 | Wolf et al. | 546/63 |
| 3,637,706 | 1/1972 | Wolf et al. | 544/361 |
| 3,647,800 | 3/1972 | Wolf et al. | 546/81 |
| 3,657,233 | 4/1972 | Wolf et al. | 544/127 |
| 3,674,790 | 7/1972 | Wolf et al. | 546/81 |
| 3,987,047 | 10/1976 | Griss et al. | 540/580 |
| 4,108,998 | 8/1978 | Demerson et al. | 514/291 |
| 4,631,286 | 12/1986 | Shutske et al. | 514/297 |
| 4,695,573 | 9/1987 | Shutske et al. | 514/290 |
| 4,762,841 | 8/1988 | Shutske | 514/278 |
| 4,816,456 | 3/1989 | Summers | 514/255 |
| 4,851,536 | 7/1989 | Skotnicki et al. | 546/106 |
| 4,897,400 | 1/1990 | Shutske | 514/289 |

FOREIGN PATENT DOCUMENTS

| | | |
|---|---|---|
| 0179383 | 4/1986 | European Pat. Off. |
| 0268871 | 6/1988 | European Pat. Off. |
| 1022940 | 3/1966 | United Kingdom ................. 546/79 |
| WO89/2739 | 4/1989 | World Int. Prop. O. |
| WO89/02740 | 4/1989 | World Int. Prop. O. |

OTHER PUBLICATIONS

Abramochkin, et al., Khim.-Farm. Zh.(English language version), vol. 4(7), pp. 10-13 (1970).
Konshin et al.(I), Khim.-Farm. Zh.(English language version), vol. 5(11), pp. 10-12 (1971).
Konshin, et al.(II), Izv. Vyssh. Ucheb. Zaved. Khim. Khim. Tekhnol.(English language version), vol. 15(2), pp. 243-244 (1972).
Konshin, et al.(III), Izv. Vyssh. Ucheb. Zaved. Khim. Khim. Tekhnol.(English language version), vol. 15(5), pp. 726-727 (1972).
Konshin, et al.(IV), Khim. Geterotzikl. Soedin.(English language version), vol. 1973 (No. 4), pp. 531-534.
Konshin, et al.(V), Khim.-Farm. Zh.,(English language version), vol. 8(7), pp. 17-19 (1974).
Konshin, Nauch. Tr. Perm. Farmstsevt. Int.(English language version), vol. 10, pp. 6-9 (1976).
Khaldeeva, et al., Khim. Getrotsikl. Soedin.(English language translation) 1976, No. 2, pp. 263-265.
Bialevsky, Coll. Czech. Chem. Commun., vol. 42, pp. 2802-2808 (1977).
Krisna, et al., Ind. J. Chem., vol. 16B(2), pp. 156-158 (1978).
Bun-Hoi, et al., Chemical Abstracts, vol. 69: 106408d (1968).
Patnaik, et al., J. Med. Chem., vol. 9, pp. 483-488 (1966).
Steinberg, et al., J. Med. Chem., vol. 18(11), pp. 1056-1061 (1975).
Ferguson, et al., Chemical Abstracts, vol. 98: 154912j (1983).
Ferguson, et al., Chemical Abstracts, vol. 102: 73854r (1985).
Flood, et al., Chemical Abstracts, vol. 103(7): 48119t (1985).
Cherkin, et al., Chemical Abstracts, vol. 100(5): 114871y (1984).

Primary Examiner—Diana Rivers
Attorney, Agent, or Firm—Tatsuya Ikeda

[57] ABSTRACT

There are disclosed novel compounds having the formula,

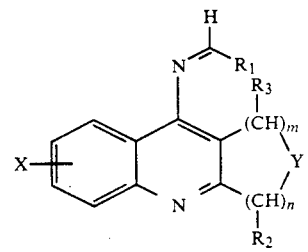

wherein,
m is an integer of 0-3;
n is an integer of 1-4;
R$_1$ is hydrogen, alkyl, cycloalkyl, arylloweralkyl, aryl, naphthyl, furyl, thienyl, pyridinyl or pyrrolyl; each R$_2$ and R$_3$ are independently hydrogen, loweralkyl or arylloweralkyl, or alternatively R$_2$ and R$_3$ taken together form a methylene or ethylene bridge;
X is hydrogen, loweralkyl, cycloalkyl, loweralkoxy, halogen, hydroxy, nitro, trifluoromethyl, formyl, loweralkoxycarbonyl, arylcarbonyl, —SH, loweralkylthio, —NHCOR$_4$ or —NR$_5$R$_6$, R$_4$ being hydrogen or loweralkyl, and R$_5$ and R$_6$ being independently hydrogen, loweralkyl or cycloalkyl;
Y is CH$_2$, CH=CH, O, S or NR$_7$, R$_7$ being hydrogen, loweralkyl or arylloweralkyl; with the proviso that the number of said methylene or ethylene bridge shall not exceed 1 and that when Y is CH$_2$, one and only one combination of R$_2$ and R$_3$ must constitute a methylene or ethylene bridge;

stereo, optical and geometrical isomers thereof, and pharmaceutically acceptable acid addition salts thereof, which are useful for enhancing memory.

19 Claims, No Drawings

N-[SUBSTITUTED ALKYLIDENE]FUSED-BICYCLOALKYLIDENE QUINOLINAMINES USEFUL FOR ENHANCING THE CHOLINERGIC FUNCTION IN A MAMMAL

This is a continuation-in-part of a co-pending prior application, Ser. No. 223,848, filed Jul. 25, 1988, which is a continuation-in-part of a prior application, Ser. No. 094,181 filed Sept. 8, 1987, now abandoned.

The present invention relates to novel compounds having the formula,

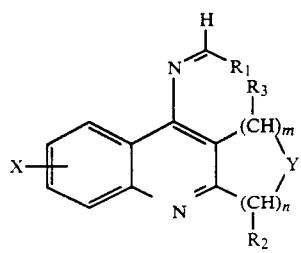

wherein,
m is an integer of 0-3;
n is an integer of 1-4;
$R_1$ is hydrogen, alkyl, cycloalkyl, arylloweralkyl, aryl, naphthyl, furyl, thienyl, pyridinyl or pyrrolyl; each $R_2$ and $R_3$ are independently hydrogen, loweralkyl or arylowralkyl, or alternatively $R_2$ and $R_3$ taken together form a methylene or ethylene bridge;
X is hydrogen, loweralkyl, cycloalkyl, loweralkoxy, halogen, hydroxy, nitro, trifluoromethyl, formyl, loweralkoxycarbonyl, arylcarbonyl, —SH, loweralkylthio, —NHCOR$_4$ or —NR$_5$R$_6$, R$_4$ being hydrogen or loweralkyl, and R$_5$ and R$_6$ being independently hydrogen, loweralkyl or cycloalkyl;
Y is CH$_2$, CH=CH, O, S or NR$_7$, R$_7$ being hydrogen, loweralkyl or arylloweralkyl; with the proviso that the number of said methylene or ethylene bridge shall not exceed 1 and that when Y is CH$_2$, one an only one combination of R$_2$ and R$_3$ must constitute a methylene or ethylene bridge;
stereo, optical and geometrical isomers thereof, and pharmaceutically acceptable acid addition salts thereof, which are useful for enhancing memory.

Throughout the specification and the appended claims, a given chemical formula or name shall encompass all stereo and optical isomers thereof where such isomers exist, as well as pharmaceutically acceptable acid addition salts thereof and solvates thereof such as for instance hydrates.

The following definitions shall apply throughout the specification and appended claims.

Unless otherwise states or indicated, the term alkyl denotes a straight or branched alkyl group having from 1 to 18 carbon atoms. Examples of said alkyl include methyl, n-propyl, iso-butyl, heptyl, decyl, dodecyl, hexadecyl and octadecyl.

Unless otherwise stated or indicated, the term loweralkyl denotes a straight or branched alkyl group having from 1 to 6 carbon atoms. Examples of said loweralkyl include methyl, ethyl, n-propyl, iso-butyl, pentyl and hexyl.

Unless otherwise stated or indicated, the term cycloalkyl denotes a saturated ring containing 3 to 7 carbon atoms. Examples of said cycloalkyl include cyclopropyl, cyclohexyl and cycloheptyl.

Unless otherwise stated or indicated, the term halogen shall mean fluorine, chlorine, or bromine or iodine.

Unless otherwise stated or indicated, the term aryl shall mean an unsubstituted phenyl group, a phenyl group substituted with 1, 2 or 3 substituents each of which being independently loweralkyl, loweralkoxy, halogen, hydroxy, trifluormethyl, phenoxy or benzyloxy.

The phrase "each R$_2$" appearing in the definition of group R$_2$ refers to the fact that when n is greater than 1, there are more than one R$_2$ group in the molecule, in which case they may or may not be the same. Similarly, the phrase "each R$_3$" appearing in the definition of group R$_3$ refers to the fact that when m is greater than 1, there are more than one R$_3$ group in the molecule in which case they may or may not be the same. The groups R$_2$ and R$_3$ may combine so as to form a methylene or ethylene bridge in the molecule, but the number of such bridge is limited to 0 or 1.

The compounds of this invention can be prepared by utilizing the synthetic scheme described below.

SYNTHETIC SCHEME

A compound of formula II is allowed to react with an aldehyde of formula III to afford compound I, where the definitions of m, n, R$_1$, R$_2$, R$_3$, X and Y are the same as given above. Typically, this reaction is conducted in a suitable solvent such as benzene, toluene or xylene at a temperature of about 80°-150° C. in the presence of a base such as piperidine, morpholine, diethylamine or diisopropylamine. The starting compound II can be prepared, for instance, by utilizing synthetic schemes disclosed in U.S. patent application, Ser. Nos. 21,8,755, filed Jul. 8, 1988; 244,212, filed Sept. 24, 1988; and 171,103, filed Apr. 4, 1988, now U.S. Pat. No. 4,843,079.

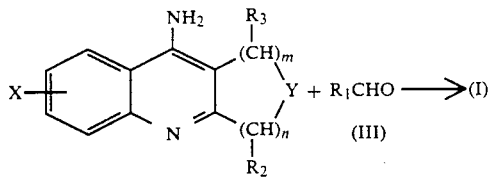

The compounds of Formula I of the present invention are useful in the treatment of various memory dysfucntions characterized by decreased cholinergic function, such as Alzheimer's disease.

This utility is manifested by the ability of these compounds to inhibit the enzyme cholinesterase and thereby increase acetylcholine levels in the brain. Further, the compounds of this invention are in general less toxic and have a broader therapetuic window than heretofore known compounds such as tacrine and physostigmine, making them more therapeutically acceptable.

The ability to inhibit acetylcholinesterase was determined by the photometric method of Ellman et al., Biochem. Pharmacol. 7,88 (1961). Results of acetylcholinesterase inhibition for some of the compounds of this invention are presented in Table 1 along with those for reference compounds.

TABLE 1

| Acetylcholinesterase Inhibition Assay | |
|---|---|
| Compound | Acetylcholinesterase Inhibition IC$_{50}$(molar) |
| 1,4-Methano-N-(phenylmethylene)-1,2,3,4-tetrahydro-9-acridinamine | $1.2 \times 10^{-5}$ |
| 1,4-Methano-N-(phenylmethylene)-6-trifluoromethyl-1,2,3,4-tetrahydro-9-acridinamine | $2.2 \times 10^{-5}$ |
| (Reference Compounds) | |
| Tacrine (9-amino-1,2,3,4-tetrahydroacridine) | $3.1 \times 10^{-7}$ |
| Physostigmine | $6.0 \times 10^{-9}$ |

This utility is further demonstrated by the ability of these compounds to restore cholinergically deficient memory in the Dark Avoidance Assay, where they are in general active over a broader dose range than heretofore known compounds, a distinct therapeutic advantage. In this assay mice are tested for their ability to remember an unpleasant stimulus for a period of twenty-four (24) hours. A mouse is placed in a chamber that contains a dark compartment; a strong incandescent light drives it to the dark compartment, where an electric shock is administered through metal plates on the floor. The animal is removed from the testing apparatus and tested again, twent-four (24) hours later, for the ability to remember the electric shock.

If scopolamine, an anticholinergic that is known to cause memory impairment, is administered before an animal's initial exposure to the test chamber, the animal re-enters the dark compartment shortly after being placed in the test chamber twenty-four (24) hours later. This effect of scopolamine is blocked by an active test compound, resulting in a greater interval before re-entry into the dark compartment.

The test results are expressed as the percent of a group of animals in which the effect of scopolamine is blocked, as manifested by an increased interval between being placed in the test chamber and re-entering the dark compartment. Results of Dark Avoidance Assay for a representative compound of this invention and physostigmine (reference compound) are presented in Table 2.

TABLE 2

| Dark Avoidance Assay | | |
|---|---|---|
| Compound | Dose (mg/kg of body weight, s.c) | % of Animals with Scopolamin Induced Memory Deficit Reversal |
| 1,4-Methano-N-(phenylmethylene)-1,2,3,4-tetrahydro-9-acridinamine | 0.31 | 27% |
| (Reference Compound) | | |
| Physostigmine | 0.31 | 20% |

Effective quantities of the compounds of the inentions may be administered to a patient by any of the various methods, for example, orally as in capsules or tablets, parenterally in the form of sterile solutions or suspensions, and in some cases intravenously in the form of sterile solutions, The free base final products, while effective themselves, may be formulated and administered in the form of their pharmaceutically acceptable acid addition salts for purposes of stability, convenience of crystallization, increased solubility and the like.

Acids useful for preparing the pharmaceutically acceptable acid addition salts of the invention include inorganic acids such as hydrochloric, hydrobromic, sulfuric, nitric, phosphoric and perchloric acids, as well as organic acids such as tartaric, citric, acetic, succinic, maleic, fumaric and oxalic acids.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compounds, but may be varies depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0–300 milligrams of active compound.

The tablets, pills, capsules, troches and the like may also contain the following ingredients: a binder such as micro-crystalline cellulose, gum tragacanth or gelatin; an excipient such as starch or lactose, a disintegrating agents such as alginic acid, Primogel, cornstarch and the like; a lubricant such as magnesium stearate or Sterotex; a glidant such as collodial silicon dioxide; and a sweetening agent such as sucrose or saccharin may be added or a flavoring agent such as peppermint, methyl salicylate, or orange flavoring. When the dosage unit form is a capsule, it may contain, in additions to materials of the above type, a liquid carrier such as a fatty oil. Other dosage unit forms may contain other various materials which modify the physical form of the dosage unit, for example, as coatings. Thus tablets or pills may be coated with sugar, shellac, or other enteric coating agents. A syrup may contain, in addition to the active compounds, sucrose as a sweetening agent and certain preservatives, dyes, coloring and flavors. Materials used in preparing these various compositions should be pharmaceutically pure and non-toxic in the amounts used.

For the purpose of parenteral therapeutic administration, the active compounds of the invention may be incorporated into a solution or suspension. These preparations should contain at least 0.1% of active compound, but may be varied between 0.5 and about 30% of the weight thereof. The amount of active compound in such compositions is such that a suitable dosage will be obtained. Preferred compositions and preparatins according to the present inventions are prepared so that a parenteral dosage unit contains between 0.5 to 100 milligrams of active compound.

The solutions or suspensions may also include the following components: a sterile diluent such as water for injections, saline solution, fixed oils, polyethylene glycols, glycerine, propylene glycol or other synthetic solvents; antibacterial agents such as benzyl alcohol or sodium bisulfite; chelating agents such as ethylenediaminetetraacetic acid; buffers such as acetates, citrates or phosphates and agents for the adjustment of tonicity such as sodium chloride or dextrose. The parenteral preparations can be enclosed in disposable syringes or multiple dose vials made of glass or plastic.

Examples of the compounds of this invention include:
1,4-methano-6-methyl-N-(phenylmethylene)-1,2,3,4-tetrahydro-9-acridinamine;

1,4-methano-N-(phenylmethylene)-6-trifluoromethyl-1,2,3,4-tetrahydro-9-acridinamine;

N-(phenylmethylene)-3,4-dihydro-1H-thiopyrano[4,3-b]quinolin-10-amine;

N-ethylidene-3,4-dihydro-1H-thiopyrano[4,3-b]quinolin-10-amine;

N-decylidene-3,4-dihydro-1H-thiopyrano[4,3-b]quinolin-10-amine;

N-(phenylmethylene)-3,4-dihydro-1H-pyrano[4,3-b]quinolin-10-amine;

N-[(4-fluorophenyl)methylene]-3,4-dihydro-1H-pyrano[4,3-b]quinolin-10-amine;

N-hexylidene-3,4-dihydro-1H-pyrano[4,3-b]quinolin-10-amine;

N-(phenylmethylene)-2,3-dihydrothieno[3,2-b]quinolin-9-amine;

N-[(2-thienyl)methyene]-2,3-dihydrothieno[3,2-b]quinolin-9-amine;

N-dodecylidene-2,3-dihydrothieno[3,2-b]quinolin-9-amine;

N-(phenylmethylene)-1,3-dihydrothieno[3,4-b]quinolin-9-amine;

N-[(4-pyridinyl)methylene]-1,3-dihydrothieno[3,4-b]quinolin-9-amine;

N-tetradecylidene-1,3-dihydrothieno[3,4-b]quinolin-9-amine;

1-phenylmethyl-N-(phenylmethylene)-2,3-dihydro-2H-pyrrolo[3,2-b]quinolin-9-amine;

N-(phenylmethylene)-2,3-dihydro-1H-pyrrolo[3,2-b]quinolin-9-amine;

2-phenylmethyl-N-(phenylmethylene)-1,3-dihydro-2H-pyrrolo[3,4-b]quinolin-9-amine;

N-(phenylmethylene)-1,3-dihydro-2H-pyrrolo[3,4-b]quinolin-9-amine;

1,4-methano-N-(phenylmethylene)-1,2,3,4-tetrahydro-9-acridinamine;

N-ethylidene-1,4-methano-1,2,3,4-tetrahydro-9-acridinamine;

N-hexadecylidene-1,4-methano-1,2,3,4-tetrahydro-9-acridinamine;

1,4-ethano-N-(phenylmethylene)-1,2,3,4-tetrahydro-9-acridinamine;

1,4-ethano-N-[(4-fluorophenyl)methylene]-1,2,3,4-tetrahydro-9-acridinamine;

N-decylidene-1,4-ethano-1,2,3,4-tetrahydro-9-acridinamine;

7-methyl-1,4-methano-N-pentylidene-1,2,3,4-tetrahydro-9-acridinamine;

1,4-methano-N-(4-methylpentylidene)-1,2,3,4-tetrahydro-9-acridinamine;

N-[(cyclopropyl)methylene]-1,4-methano-1,2,3,4-tetrahydro-9-acridinamine;

N-[(cyclopentyl)methylene]-1,4-methano-1,2,3,4-tetrahydro-9-acridinamine;

N-[(cyclohexyl)methylene]-1,4-ethano-1,2,3,4-tetrahydro-9-acridinamine;

1,4-ethano-N-[(4-fluorophenyl)methylene]-1,2,3,4-tetrahydro-9-acridinamine;

1,4-ethano-N-octylidene-1,2,3,4-tetrahydro-9-acridinamine; and 7-chloro-1,4-ethano-N-(phenylmethylene)-1,2,3,4-tetrahydro-9-acridinamine;

The following examples are presented in order to illustrate this invention.

EXAMPLE 1

1,4-Methano-1,2,3,4-tetrahydro-9-acridinamine

Anthranilonitrile (2.40 g) was mixed together with norcamphor (4.40 g) and then 4.0 g of freshly fused $ZnCl_2$ was added and the reaction mixture was heated at 120° C. After 1.5 hours it became so thick that it could not be stirred, so 10 ml of 1,2-dichloroethane was added and the reaction mixture was refluxed for 1 hour. At the end of this time, 40 ml of 10% NaOH was added and the mixture was stirred overnight. It was then extracted several times with 2-butanone which gave a crude product that was purified by flash chromatography (EtOAc, then 5% $Et_2NH$/EtOAc) to give 3.04 g of foam. Recrystallization from $CH_2Cl_2$/pentane gave 2.30 g of analytically pure product, m.p. 186°–188°.

ANALYSIS: Calculated for $C_{14}H_{14}N_2$: 79.96%C, 6.71%H, 13.33%N, Found: 79.85%C, 6.65%H, 13.13%N.

EXAMPLE 2

1,4-Methano-N-(phenylmethylene)-1,2,3,4-tetrahydro-9-acridinamine 1,4-Methano-1,2,3,4-tetrahydro-9-acridinamine (8.40 g) was refluxed in 300 ml of toluene that contained 7.0 g of morpholine and 6.4 g of benzaldehyde that had been freshly washed with aqueous $K_2CO_3$. The reaction mixture was refluxed overnight and then concentrated and purified by flash chromatography (20% EtOAc/$CH_2Cl_2$) to give 9.51 g of chromatographically pure product. Analytically pure material was obtained by recrystallization from benzene/pentane, m.p. 128°–130° C.

ANALYSIS: Calculated for $C_{21}H_{18}N_2$: 84.53%C, 6.08%H, 9.39%N, Found: 84.49%C, 6.02%H, 9.31%N.

EXAMPLE 3

1,4-Methano-6-methyl-1,2,3,4-tetrahydro-9-acridinamine

A solution of 2-amino-4-methylbenzonitrile (16.0 g) and zinc chloride (24.7 g) in 70 ml of nitrobenzene was heated at 50° C. for 1hour. To this was added norcamphor (20.0 g) and the mixture was stirred at 130° C. for 3 hours. The reaction mixture was cooled and diluted with ether and the zinc complex was filtered. This complex was partitioned between aqueous $NH_4OH$ and 2-butanone (MEK) and the aqueous phase was extracted with MEK. The organics were washed with water, dried (saturated NaCl,$MgSO_4$) and concentrated to an oil which was triturated with ether to give 12.8 g of white powder, m.p. 159°–162° C. A 4.0 g portion was recrystallized from isopropyl ether to give 2.5 g of analytically pure white solid, m.p. 162°–164° C.

ANALYSIS: Calculated for $C_{15}H_{16}N_2$: 80.32%C, 7.19%H, 12.49%N, Found: 80.29%C, 7.05%H, 12.52%N.

EXAMPLE 4

1,4-Methano-6-methyl-N-(phenylmethylene)-1,2,3,4-tetrahydro-9-acridinamine

A solution prepared from 1,4-methano-6-methyl-1,2,3,4-tetrahydro-9-acridinamine (8.6 g), benzaldehyde (6.3 g, freshly washed with $K_2CO_3$ solution), morpholine (6.9 ml) and toluene (300 ml) was refluxed, with removal of water, for eighteen (18) hours. At this time, 6.3 g of benzaldehyde was added and reflux was continued for twenty-four (24) hours. The solvent was then removed in vacuo and the imine was purified via flash chromatography (DCM) to give 7.3 g of an organish solid, m.p. 144°–147° C. A 3.5 g portion was recrystallized from isopropyl ether to give 2.54 g of light yellow crystals, m.p. 149°–152° C.

ANALYSIS: Calculated for $C_{22}H_{20}N_2$: 84.58%C, 6.45%H, 8.97%N, Found: 84.46%C, 6.42%H, 9.00%N.

EXAMPLE 5

1,4-Methano-1,2,3,4-tetrahydro-6-trifluoromethyl-9-acridinamine

To a solution of 2-amino-4-trifluoromethylbenzonitrile (12.8 g) in 50 ml of nitrobenzene was added freshly fused and pulverized $ZnCl_2$ (14.1 g). This was heated at 50° C. for 1 hour and to this mixture was added norcamphor (11.4 g). The reaction mixture was heated at 130° C. for 3 hours, after which it was cooled, diluted with ethyl ether and filtered. The resulting solid was partitioned between 2-butanone (MEK) and aqueous $NH_4OH$ and the aqueous portion was extracted with MEK. The combined organics were washed with water, dried (saturated NaCl, $MgSO_4$) and concentrated to a solid which was triturated with ether/hexane to give 10.3 g of a white powder, m.p. 174°–179° C. A 4.0 g portion was recrystallized from methanol/water to give 3.5 g of an analytically pure white powder, m.p. 175°–178° C.

ANALYSIS: Calculated for $C_{15}H_{13}F_3N_2$: 64.74%C, 4.71%H, 10.07%N, Found: 64.70%C, 4.88%H, 10.09%N.

EXAMPLE 6

1,4-Methano-N-(phenylmethylene)-6-trifluoromethyl-1,2,3,4-tetrahydro-9-acridinamine A mixture prepared from 1,4-methano-1,2,3,4-tetrahydro-6-trifluoromethyl-9-acridinamine (7.65 g), benzaldehyde (4.4 g, freshly washed with $K_2CO_3$), morpholine (4.8 ml) and toluene (300 ml) was refluxed with removal of water for eighteen (18) hours. At this point, an additional 4.4 g of benzaldehyde was added and reflux was continued for twenty-four (24) hours.

The reaction was then concentrated to a solid and the residue was chromatographed (DCM) to give 8.3 g of an orangish solid, m.p. 120°–126° C. A 4.07 g portion was recrystallized from cyclohexane to give 2.56 g of an off-white solid, m.p. 127°–130° C.

ANALYSIS: Calculated for $C_{22}H_{17}F_3N_2$: 72.12%C, 4.68%H, 7.65%N, Found: 72.15%C, 4.83%H, 7.61%N.

EXAMPLE 7

3,4-Dihydro-1H-thiopyrano[4,3]quinolin-10-amine

Tetrahydrothiopyran-4-one (10.0 g) was mixed with anthranilonitrile (5.08 g) and the mixture warmed at 60° C. until a homogeneous solution was obtained. Freshly fused $ZnCl_2$ (8.2 g) was then added portionwise and the temperature of the reaction mixture raised to 120° C. After two (2) hours it was cooled and distributed between 10% NaOH and 2-butanone. The organic phase was separated, dried and concentrated, and the crude product triturated with $Et_2O$ and then passed over a silica gel column (5% $Et_3N$/ethyl acetate). The product-containing fractions were concentrated and the product recrystallized from toluene to give 3.66 g, m.p. 214°–216° C.

ANALYSIS: Calculated for $C_{12}H_{12}N_2S$: 66.63%C, 5.59%H, 12.95%N, Found: 66.74%C, 5.71%H, 12.79%N.

EXAMPLE 8

N-(Phenylmethylene)-3,4-dihydrothiopyrano-1H-[4,3-b]quinolin-10-amine 3,4-Dihydrothiopyrano-1H-[4,3-b]quinolin-10-amine (8.64 g) was suspended in 300 ml of toluene to which morpholine (7.0 g) and benzaldehyde (freshly washed with aqueous $K_2CO_3$ solution, 8.50 g) were then added. The reaction mixture was refluxed overnight with removal of water (Dean-Stark trap) and then concentrated and purified by flash chromatography (20% EtOAc/$CH_2Cl_2$). The product-containing fractions were concentrated to give 7.30 g of chromatographically pure product, m.p. 171°–173° C. Analytically pure material was obtained by recrystallization from $CH_2Cl_2$/pentane, m.p. 175°–176° C.

ANALYSIS: Calculated for $C_{19}H_{16}N_2S$: 74.96%C, 5.30%H, 9.20%N, Found: 74.97%C, 5.25%H, 9.18%N.

EXAMPLE 9

1,4-Dihydro-1,4-ethano-9-acridinamine

A mixture prepared from anthranilonitrile (4.18 g), freshly fused zinc chloride (7.2 g) and 15 ml of nitrobenzene was heated at 50° C. for 45 minutes. To the resulting suspension was added bicyclo[2.2.2]oct-2-en-5-one (6.5 g) and this was heated at 130° C. for 1.5 hours.

The reaction mixture was cooled and treated with ethyl ether, and the precipitate was filtered, rinsed with ether and then partitioned between 2-butanone (MEK) and aqueous $NH_4OH$ solution. The aqueous phase was extracted with MEK and the combined organics were washed with water and dried (saturated NaCl, $MgSO_4$). Removal of the solvents gave 5.7 g of an off-white powder which was recrystallized from methanol/water to give 4.76 g of an off-white solid, m.p. 218°–220° C. d.

ANALYSIS: Calculated for $C_{15}H_{14}N_2$: 81.05%C, 6.35%H, 12.60%N, Found: 80.96%C, 6.34%H, 12.65%N.

EXAMPLE 10

1,4-Dihydro-1,4-ethano-N-(phenylmethylene)-9-acridinamine

A mixture of 1,4-dihydro-1,4-ethano-9-acridinamine (11.4 g), benzaldehyde (8.2 g, freshly washed with $K_2CO_3$ solution) and morpholine (9.0 ml) in 350 ml toluene was refluxed with removal of water for eighteen (18) hours. An additional 6 g of benzaldehyde was added and reflux was continued for twelve (12) hours with removal of water.

The reaction mixture was concentrated, passed through a column of florisil (DCM) and the imine was purified via flash chromatography (DCM then 5% EtOAc/DCM) to give 13.4 g of an orangish solid. A 3.0 g portion was recrystallized from methanol/water to give 2.54 g of light yellow crystals, m.p. 178°–180° C.

ANALYSIS: Calculated for $C_{22}H_{18}N_2$: 85.13%C, 5.85%H, 9.02%N, Found: 85.03%C, 6.05%H, 8.94%N.

We claim:

1. A compound of the formula

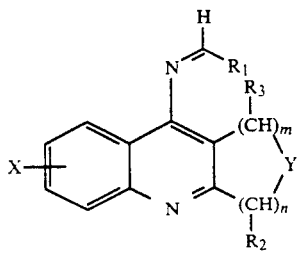

wherein
- m is an integer of 1–3;
- n is an integer of 1–4;
- $R_1$ is hydrogen, alkyl, cycloalkyl, arylloweralkyl, aryl, naphthyl, furyl, thienyl, pyridinyl or pyrrolyl;
- each $R_2$ and $R_3$ is independently hydrogen, loweralkyl or arylloweralkyl, except that one and only one combination of $R_2$ and $R_3$ must constitute a methylene or ethylene bridge;
- X is hydrogen, loweralkyl, cycloalkyl, loweralkoxy, halogen, hydroxy, nitro, trifluoromethyl, formyl, loweralkylcarbonyl, arylcarbonyl, —SH, loweralkylthio, —NHCOR$_4$ or —NR$_5$R$_6$, R$_4$ being hydrogen or loweralkyl, and R$_5$ and R$_6$ being independently hydrogen, loweralkyl or cycloalkyl;
- Y is CH$_2$, or CH=CH;

a stereo, optical and geometrical isomer thereof, or a pharmaceutically acceptable acid addition salt thereof.

2. The compound as defined in claim 1, which is 1,4-methano-N-(phenylmethylene)-1,2,3,4-tetrahydro-9-acridamine.

3. The compound as defined in claim 1, which is 1,4-methano-6-methyl-N-(phenylmethylene)-1,2,3,4-tetrahydro-9-acridinamine.

4. The compound as defined in claim 1, which is 1,4-methano-N-(phenylmethylene)-6-trifluoromethyl-1,2,3,4-tetrahydro-9-acridinamine.

5. The compound as defined in claim 1, which is 1,4-dihydro-1,4-ethano-N-(phenylmethylene)-9-acridinamine.

6. The compound as defined in claim 1, which is 7-methyl-1,4-methano-N-pentylidene-1,2,3,4-tetrahydro-9-acridinamine.

7. The compound as defined in claim 1, which is N-hexylidene-1,4-methano-1,2,3,4-tetrahydro-9-acridinamine.

8. The compound as defined in claim 1, which is 1,4-methano-N-(4-methylpentylidene)-1,2,3,4-tetrahydro-9-acridinamine.

9. The compound as defined in claim 1, which is N-[(cyclopropyl)methylene]-1,4-methano-1,2,3,4-tetrahydro-9-acridinamine.

10. The compound as defined in claim 1, which is N-[(cyclopentyl)methylene]-1,4-methano-1,2,3,4-tetrahydro-9-acridinamine.

11. The compound as defined in claim 1, which is 1,4-ethano-N-(phenylmethylene)-1,2,3,4-tetrahydro-9-acridinamine.

12. The compound as defined in claim 1, which is N-[(cyclohexyl)-methylene]-1,4-ethano-1,2,3,4-tetrahydro-9-acridinamine.

13. The compound as defined in claim 1, which is 1,4-ethano-N-[(4-fluorophenyl)methylene]-1,2,3,4-tetrahydro-9-acridinamine.

14. The compound as defined in claim 1, which is 1,4-ethano-N-octylidene-1,2,3,4-tetrahydro-9-acridinamine.

15. The compound as defined in claim 1, which is 7-chloro-1,4-ethano-N-(phenylmethylene)-1,2,3,4-tetrahydro-9-acridinamine.

16. A pharmaceutical composition for enhancing the cholinergic function in a mammal which comprises an effective amount of a compound as defined in claim 1 and a suitable carrier therefor.

17. The pharmaceutical composition as defined in claim 16 which comprises 1,4-methano-N-(phenylmethylene)-1,2,3,4-tetrahydro-9-acridinamine.

18. A method of increasing the cholinergic function in a mammal which comprises administering to the mammal an effective cholinergic function enhancing amount of a compound as defined in claim 1.

19. The method as defined in claim 18, which comprises the administration of 1,4-methano-N-(phenylmethylene)-1,2,3,4-tetrahydro-9-acridinamine.

* * * * *